United States Patent [19]
Merkle et al.

[11] Patent Number: 5,763,659
[45] Date of Patent: Jun. 9, 1998

[54] PREPARATION OF OPTICALLY ACTIVE 2-HALOPROPIONIC ACIDS

[75] Inventors: Hans Rupert Merkle, Ludwigshafen; Erich Fretschner, Neckarsteinach; Hanspeter Hansen, Ludwigshafen; Bernhard Zipperer, Dirmstein, all of Germany

[73] Assignee: BASF Aktiengesellschaft, Ludwigshafen, Germany

[21] Appl. No.: 860,085

[22] PCT Filed: Jan. 4, 1996

[86] PCT No.: PCT/EP96/00012

§ 371 Date: Jan. 7, 1997

§ 102(e) Date: Jan. 7, 1997

[87] PCT Pub. No.: WO96/22272

PCT Pub. Date: Jul. 25, 1996

[30] Foreign Application Priority Data

Jan. 19, 1995 [DE] Germany ................. 195 01 452.9

[51] Int. Cl.$^6$ ............................................. C07C 53/15
[52] U.S. Cl. ............................................. 572/602
[58] Field of Search ............................................. 562/602

[56] References Cited

U.S. PATENT DOCUMENTS

| 5,049,676 | 9/1991 | Metivier et al. |
| 5,278,054 | 1/1994 | Buchner et al. |

FOREIGN PATENT DOCUMENTS

| 196 625 | 10/1986 | European Pat. Off. |
| 257 716 | 3/1988 | European Pat. Off. |
| 401 104 | 12/1990 | European Pat. Off. |
| 511 526 | 11/1992 | European Pat. Off. |
| 2 459 221 | 1/1981 | France |
| 41 17 255 | 12/1992 | Germany |
| 93/22269 | 11/1993 | WIPO |

OTHER PUBLICATIONS

Chem. Abst. JP 2 104 560, 1990.
Chem. Abst. JP 71 068 445, 1986.
Chem. Abst JP 61 057 534, 1986.
Pure and Appl. Chem. 62, 1441, 1990.
S. K. Dahod et al., Biotech. and Bioeng. vol. 30, No. 5, Oct. 5, 1987.
Appl. Biochem. Biotech. 9 (3), 1984, 255.
J. Am. chem. Soc. 107, 7072 (1985).
Bio. Med. Chem. Lett. 1991 I, 339.
Chiral Synthons by Biocatalysis, Taylor, 157–165.
J. of Gen. Microbiology 128, 1755, 1982.
Chem. Abst. JP 61 111 699, 1986.
Chem. Abst. JP 57 094 295, 1983.
Chem. Abst. JP 62 205 797, 1987.

*Primary Examiner*—Paul J. Killos
*Attorney, Agent, or Firm*—Keil & Weinkauf

[57] ABSTRACT

The present invention relates to a process for the preparation of optically active 2—halopropionic acids, in which the corresponding optically active alkyl 2—halopropionates are caused to react with a carboxylic acid at elevated temperature in a transacylation reaction with the formation of the optically active 2—halopropionic acid and the alkyl carboxylate, and the optically active 2—halopropionic acid obtained is separated from the reaction mixture. The optically active products produced are important intermediates for the preparation of plant protectants and pharmaceuticals.

11 Claims, No Drawings

PREPARATION OF OPTICALLY ACTIVE 2-HALOPROPIONIC ACIDS

The present invention relates to a novel process for the preparation of optically active 2-halopropionic acids.

It is known to be possible to prepare l-2-chloropropionic acid and the sodium salt thereof by alkaline hydrolysis of isobutyl l-2-chloropropionate. During this process however, a poor-quality product (ca 90 to 95 % of excess enantiomer) is often formed, which still contains 5 to 10 % of lactic acid as by-product.

FR 2,700,164 describes the synthesis of l-2-chloropropionates by causing o-silylized silylized ketenacetals to react with N-chlorosuccinimide and the hydrolysis thereof with alkali metal hydroperoxides to form l-2-chloropropionic acid.

JP 57/094295, JP 62/205797, EP-A 196,625, JP 61/111699 reveal that it is possible to dissociate racemic 2-chloropropionates enantio-selectively by means of enzymes. However, a disadvantage of this is, apart from the maximum possible yield of only 50 % - based on racemate -, the insufficient enantiomer purity of the 2-chloropropionates formed.

The racemate dissociation of 2-halocarboxylates by lipase from candida cylindracea is also known (US 898,972).

According to Bio. Med. Chem. Lett. 1991 1 339, optically active phenoxypropionates are obtained by enzymatic esterification of the corresponding racemic acids, one of the enantiomers being esterified whilst the other remains as acid, depending on the enzyme used. Separation of the optically active compounds is then carried out by distillation and/or extraction. Depending on process conditions used concentrations of the d- or l-isomers of from 70 % to ca 95 % are obtained.

In the case of enzymatic dehalogenation of racemic chloropropionic acid, the d-enantiomer is converted into lactic acid and the l-chloropropionic acid remains unchanged. The maximum possible yields are approximately 50 % —based on racemate —(Biocatalysis, D.A. Abramowicz CZ (Ed) van Nostrand R. N.Y. (1990), Journal of General Microbiology 128, 1755 (1982)).

Furthermore, EP-A 257,716 discloses a continuous process in which methyl d,l-2- bromopropionate is used as racemate and is converted into methyl l-(-)-2- bromopropionate by means of Candida cylindracea lipase in a two-phase system. However no hydrolysis products are isolated in this process. Moreover S. K. Dahod and P. Sinta-Mangano in Biotechnol. Bioeng. 30 (8), 995 (1987) describe the lipase-catalyzed hydrolysis of methyl l-2-chloropropionate in the presence of carbon tetrachloride. The disadvantage of this method is, apart from the use of a chlorinated solvent, the low yield of ca 30 % at an enantiomer purity of only 95 %.

In addition, EP-A 511,526 describes a process for the enzymatic hydrolysis of racemic 2-chloropropionates in a two-phase system comprising water and a substantially water-immiscible organic solvent for the ester. This process is very elaborate, since the organic phase must a number of times be separated, brought into contact with the hydrolase, and recycled. Since only incomplete conversion takes place and no enantiomer-pure products are obtained despite relative long reaction times, this method is unsuitable for commercial manufacture of l-2- chloropropionic acid and the sodium salt thereof.

Other processes for the preparation of optically active 2-halocarboxylic acids are racemate dissociations of 2-halocarboxamides with microorganisms such as pseudomones (DE 4,117,255 A1) and 2-halocarboxylic acid nitrites by means of microorganisms (Pure and Appl. Chem. 62, 1441 (1990)).

Thus the object of the present invention is to provide a simple process for the preparation of optically active 2-halopropionic acids having as high a chemical and optical purity as possible (at least ca 98 % excess enantiomer).

Accordingly, we have found a process for the preparation of optically active 2- halopropionic acids, wherein the corresponding optically active alkyl 2-halopropionates are caused to react with a carboxylic acid at elevated temperature in a transacylation reaction with the formation of the optically active 2-halopropionic acid and the alkyl carboxylate, and the optically active 2-halopropionic acid obtained is separated from the reaction mixture.

The process of the invention is described with reference to the following reaction equation

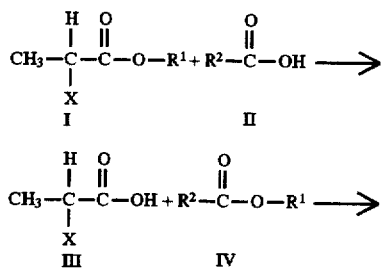

In which I is the optically active alkyl 2-halopropionate in which X denotes halogen, II is the carboxylic acid, III is the optically active 2-halopropionic acid obtained, and IV is the alkyl carboxylate formed during transacylation.

Generally, in the optically active alkyl 2-halopropionates I and 2-halopropionic acids III, X denotes chlorine, bromine, or iodine, preferably chlorine or bromine and more preferably chlorine.

In the reaction equation given above $R^1$ generally denotes $C_1$-$C_8$ alkyl, preferably $C_1$-$C_6$ alkyl, and $R^2$ generally denotes hydrogen or $C_1$-$C_4$ alkyl.

The carboxylic acids II used are advantageously formic acid, acetic acid, and propionic acid, preferably formic acid or acetic acid and more preferably formic acid.

The preparation of the optically active alkyl 2-halopropionates to be used as starting product is advantageously carried out starting from the corresponding optically active lactates by halogenation thereof. For example, the preparation of alkyl l-2-chloropropionates is carried out by halogenation of the corresponding alkyl d-lactates by replacing the hydroxyl group by chlorine. The alkyl d-lactates may be chlorinated in known manner (cf eg EP-A 401,104, JP 61/057534 (1986), JP 02/104560 (1990), JP 61/068445 (1986) and FR-A 2,459,221). The chlorination is preferably carried out using thionyl chloride in the presence of a catalyst such as N,N-dimethylformamide, inversion taking place at the asymmetrical C atom. The crude product is separated from the high-boiling fractions and then purified by distillation.

Using the procedure described above, isobutyl l-2-chloropropionate, for example, can be obtained having a chemical purity of ca 98 to 99.8 %. The optical purity (l:d) is approximately 98:2 to 100:0 %.

To effect the transacylation of the invention, the optically active alkyl 2- halopropionates may alternatively be used without previous purification.

The reaction for the preparation of the optically active 2-halopropionic acids is advantageously carried out at temperatures ranging from 40 dc to 200 dc, preferably from 80 dc to 150 dc and very advantageously at the boiling point of the carboxylic acid used for transacylation or at the boiling point of the alkyl carboxylate formed during transacylation. The reaction can be carried out under reduced, standard, or elevated pressure. It is general to operate at pressures ranging from 0.1 to 10 bar, preferably from 0.5 to 3 bar.

The carboxylic acid to be used for the transacylation can be used in the stoichiometric amount based on alkyl 2-halopropionate used. Preferably however, the carboxylic acid is used in excess, generally an excess of 10% to 5000%, preferably 200% to 1000%.

The carboxylic acid can be initially present together with the alkyl 2- halopropionate or alternatively it can be added during the transacylation reaction 20 or a portion thereof can be initially present and the remainder added during the transacylation reaction.

It may be advantageous to carry out the reaction in the presence of an acid catalyst. Suitable acid catalysts are, eg, mineral acids such as phosphoric acid, hydrohalic acids, sulfuric acid, organic sulfonic acids such as p-toluenesulfonic acid, ion exchangers in hydrogen form, and Lewis acids. Sulfuric acid is particularly suitable generally, the catalysts are used in amounts ranging from 0.1 wt% to 10 wt%, based on the alkyl 2-halopropionate.

It may also be advantageous to add small amounts of water during the transacylation reaction, generally amounts ranging from 0 wt% to 50 wt%, preferably from 0.01 wt% to 30 wt%, based on the alkyl 2-halopropionate, whilst the amount of water can be less or can be entirely omitted when use is made of formic acid as carboxylic acid, since formic acid partly decomposes under the 3s reaction conditions with the formation of water. Most of the water is usually separated concomitantly with the removal, by distillation, of the alkyl carboxylate formed.

The process is usually carried out without the use of added solvent, but solvents which are inert under the reaction conditions such as chlorinated hydrocarbons, aliphatic hydrocarbons such as hexane, or aromatic hydrocarbons such as toluene and xylene may be used as diluents if desired.

It may be advantageous to separate the alkyl carboxylate formed during transacylation during the reaction at the rate at which it is formed, advantageously by distillation.

Purification of the reaction mixture to effect isolation of the optically active 2- halopropionic acid is usually carried out by fractional distillation. This is carried out for example by separating the alkyl carboxylate formed during transacylation and any carboxylic acid still present from the reaction mixture by removal by distillation, thus obtaining the optically active 2-halopropionic acid as residue. The crude product obtained as residue can then be isolated as pure product by further purification, advantageously by distillation.

The distillations described above may be carried out under standard pressure conditions, in vacuo, or under superatmospheric pressure. If the transacylation is carried out using acid catalysts, the acid catalysts are advantageously separated or neutralized prior to distillation, eg, by the addition of alkali metal or alkaline earth metal hydroxides or alkali metal salts of weaker acids such as alkali metal formates and alkali metal acetates such as sodium formate and sodium acetate.

In the transacylation of the invention the optically active 2-halopropionic acids are obtained in a very economical manner in high yield and high optical purity.

During the synthesis and purification steps, the optical purity is retained or is only slightly reduced. The optically active 2-chloropropionic acids are starting materials in synthesis processes for pharmaceuticals and plant protectants, eg, in synthesis processes for optically active aryloxypropionic acids such as d-2,4-dichlorophen- oxypropionic acid, d-2-methyl-4-chlorophenoxypropionic acid, butyl-2-(4-[5-(trifluoromethyl)-2-pyridinyl]oxy)phenoxy propionate (Fluazifopbutyl), and ethyl-2- [4-[(6-chloro-2-benzoxazolyl)oxy]phenoxy]propionate (Fenoxaprop-ethyl).

The following examples illustrate the invention.

Example 1

493.5 g (3.0 mol ) of isobutyl l-2-chloropropionate (d: 0.8 % l: 99.2 %) and 138 g (3.0 mol) of formic acid (100% strength) are placed in a flask together with 5.6 g (0.057 mol) of sulfuric acid (100 % strength). A solution of 552 g (12 mol) of formic acid (100 % strength) and 5.6 g (0.057 mol) of sulfuric acid (100 % strength) is metered in under reflux (112°C.) over a period of 3 h. Via a column, an azeotrope comprising isobutyl formate, formic acid and water is simultaneously distilled off from the reaction flask. On completion of the addition, stirring of the reaction solution is continued for a further 2 h at the boil. On removal, by distillation, of the said azeotrope, the temperature rises to 115°C. The material in the reaction flask is neutralized with 15.5 g (0.228 mol) of sodium formate and then fractionally distilled. There are obtained 308.6 g of l-2-chloropropionic acid (d: 0.8 % l: 99.2 %) having a degree of purity of 99.8 % (GC) $bp_{40}$: 102° C.; equivalent to a yield of 94.6 % of theory.

Example 2

493.5 g (3.0 mol) of isobutyl l-2-chloropropionate (d: 0.8 % l: 99.2 %) and 138 g (3.0 mol) of formic acid (100 % strength) are placed in a flask together with 5.6 g (0.057 mol) of sulfuric acid (100% strength). A solution of 306.7 g (6 mol) of is formic acid (90 % strength) and 5.6 g (0.057 mol) of sulfuricacid(100% strength) is metered in under reflux (112° C.) over a period of 3 h. Via a column, an azeotrope comprising isobutyl formate, formic acid and water is simultaneously distilled off from the reaction flask. On completion of the addition, stirring is continued for a further 2 hours at the boil and distillation continued. During this phase, the temperature rises to 115° C. The material in the reaction flask is neutralized with 15.5 g (0.228 mol) of sodium formate and then fractionally distilled. There are obtained 305.4 g of l-2- chloropropionic acid (d: 0.9% l: 99.1 %) having a degree of purity of 99.9 % (GC) $bp_{40}$: 102° C.; equivalent to a yield of 93.7 % of theory.

Example 3

329 g (2.0 mol) of isobutyl l-2-chloropropionate (d: 0.8 % l: 99.2 %) and 230 g (5.0 mol) of formic acid (100 % strength) are placed in a flask together with 3.4 g (0.035 mol) of sulfuric acid (100 % strength). A solution of 360 g (10 mol) of formic acid (100 % strength) and 3.4 g (0.035 mol) of sulfuric acid (100 % strength) is metered in under reflux (112° C.) over a period of 3.5 h. Via a column, an azeotrope comprising isobutyl formate, formic acid and water is simultaneously distilled off from the reaction flask. On completion of the addition, stirring is continued for a further 2 hours at the boil and distillation continued. During this phase, the temperature rises to 116° C. The material in the reaction flask is neutralized with 9.52 g (0.14 mol) of sodium formate and then fractionally distilled. There are obtained 205 g of l-2- chloropropionic acid (d: 0.9% l: 99.1 %) having a degree of purity of 99.8 % (GC) $bp_{32}$: 97° C.; equivalent to a yield of 94.3 % of theory.

Example 4

164.5 g (1.0 mol) of isobutyl l-2-chloropropionate (d: 0.8% l: 99.2 %) and 333 g (5.0 mol) of acetic acid (90 % strength) are placed in a flask together with 3.68 g (0.036 mol) of sulfuric acid (96% strength). 6669 (10 mol) of aqueous acetic acid (90 %) are metered in over a period of 6 hours at 110° C. to 115° C. At the same time, an azeotrope comprising isobutyl acetate and water is distilled off from the reaction flask via a column. The material in the reaction flask is then neutralized with 5.9 g (0.072 mol) of sodium acetate and fractionally distilled. There are obtained 100 g of l-2-chloropropionic acid (d: 1 .0 % l: 99.0 %) having a degree of purity of 99.8 % (GC) $bp_{54}$: 107° C.; equivalent to a yield of 92.0 % of theory.

Example 5

3299 (2.0 mol) of isobutyl l-2-chloropropionate (d: 0.8 % l: 99.2 %) and 625 g (10 mol) of acetic acid (96 % strength) are placed in a flask together with 11 g (0.108 mol) of sulfuric acid (96% strength). 666 g (10 mol) of aqueous acetic acid (90 % strength) are metered in over a period of 7.5 hours at 114° C. to 120° C. At the same time, an azeotrope comprising isobutyl acetate and water is distilled off from the reaction flask via a column. Stirring is then continued for a further 2.5 hours at 120° C. and azeotrope is distilled off. The remaining reaction mixture is neutralized with 17.7 g (0.216 mol) of sodium acetate and fractionally distilled. There are obtained 206.89 of l-2- chloropropionic acid (d: 1.0% l: 99.0 %) having a degree of purity of 99.7 % (GC) $bp_{47}$: 104° C.; equivalent to a yield of 95.0 % of theory.

Example 6

122.5 g (1 mol) of methyl d-2-chloropropionate (d: 99% l: 1 %) and 138 g (3 mol) of formic acid (100 % strength) are placed in a flask together with 5.5 g (0.054 mol) of sulfuric acid (96% strength). A solution of 300 g (3.5 mol) of formic acid (100 % strength) and 2.9 g (0.0284 mol) of sulfuric acid (96 % strength) is metered in under reflux (102° C.) over a period of 75 minutes. Via a column, an azeotrope comprising methyl formate, formic acid and water is simultaneously distilled off from the reaction flask. On completion of the addition, stirring is continued for half an hour at the boil and distillation continued. During this phase, the temperature rises to 106° C. The material in the reaction flask is neutralized with 11.2 g (0.165 mol) of sodium formate and then fractionally distilled. There are obtained 193 g of d-2-chloropropionic acid (d: 99% l: 1 %) having a degree of purity of 99.4% (GC), $bp_{62}$: 109° C.; equivalent to a yield of 94.4 % of theory.

We claim:

1. A process for the preparation of optically active 2-halopropionic acids, wherein the corresponding optically active alkyl 2-halopropionates are caused to react with a carboxylic acid at elevated temperature in a transacylation reaction with the formation of the optically active 2-halopropionic acid and the alkyl carboxylate, and the optically active 2-halopropionic acid obtained is separated from the reaction mixture.

2. A process as defined in claim 1, wherein the reaction is carried out at temperatures ranging from 40° C. to 200° C.

3. A process as defined in claim 1, wherein the optically active 2-halopropionic acid obtained is separated from the reaction mixture by separating the alkyl carboxylate formed during transacylation and any carboxylic acid still present from the reaction mixture by distillation, thus obtaining the optically active 2-halocarboxylic acid as bottoms.

4. A process as defined in claim 1, wherein the reaction is carried out at the boiling point of the carboxylic acid used for the transacylation or at the boiling point of the alkyl carboxylate formed during transacylation.

5. A process as defined in claim 1, wherein the alkyl carboxylate formed during transacylation is distilled off.

6. A process as defined in claim 1, wherein the reaction is carried out under pressures ranging from 0.1 to 10 bar.

7. A process as defined in claim 1, wherein the optically active 2- halopropionic acid obtained is isolated from the reaction mixture formed after transacylation by subjecting the reaction mixture to fractional distillation.

8. A process as defined in claim 1 , wherein the carboxylic acid is used in excess.

9. A process as defined in claim 1, wherein the reaction is carried out in the presence of an acid catalyst.

10. A process as defined in claim 1, wherein a solvent which is inert under the reaction conditions is additionally used.

11. A process as defined in claim 1, which is used for the preparation of optically active 2-chloropropionic acids.

* * * * *

UNITED STATES PATENT AND TRADEMARK OFFICE
CERTIFICATE OF CORRECTION

PATENT NO.: 5,763,659

DATED: June 9, 1998

INVENTOR(S): MERKLE et al.

It is certified that error appears in the above-identified patent and that said Letters Patent is hereby corrected as shown below:

On the cover page, item [86], the § 371 and § 102(e) dates should be --Jul. 1, 1997--.

Signed and Sealed this

Twenty-ninth Day of September, 1998

*Attest:*

BRUCE LEHMAN

*Attesting Officer*    *Commissioner of Patents and Trademarks*